US00PP26910P2

(12) United States Plant Patent
van Gaalen

(10) Patent No.: US PP26,910 P2
(45) Date of Patent: Jul. 5, 2016

(54) ***PHLOX* PLANT NAMED 'GOLDMINE IMP'**

(50) Latin Name: *Phlox paniculata*
Varietal Denomination: Goldmine Imp

(71) Applicant: Rene van Gaalen, Rijswijk (NL)

(72) Inventor: Rene van Gaalen, Rijswijk (NL)

( * ) Notice: Subject to any disclaimer, the term of this patent is extended or adjusted under 35 U.S.C. 154(b) by 44 days.

(21) Appl. No.: 14/121,654

(22) Filed: Oct. 1, 2014

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — C. A. Whealy

(57) ABSTRACT

A new and distinct *Phlox* plant named 'Goldmine Imp', characterized by its upright plant habit; green and yellow variegated leaves with undulate margins; and red purple-colored flowers.

3 Drawing Sheets

Botanical designation: *Phlox paniculata.*
Cultivar denomination: 'GOLDMINE IMP'.

BACKGROUND OF THE INVENTION

The present invention relates to a new and distinct *Phlox* plant, botanically known as *Phlox paniculata* and hereinafter referred to by the name 'Goldmine Imp'.

The new *Phlox* plant is a naturally-occurring whole plant mutation of the *Phlox paniculata* 'Goldmine', disclosed in U.S. Plant Pat. No. 12,070. The new *Phlox* plant was discovered and selected by the Inventor as a single flowering plant within a population of plants of 'Goldmine' in a controlled greenhouse environment in Rijswijk, The Netherlands in December, 2013.

Asexual reproduction of the new *Phlox* plant by vegetative cuttings in a controlled greenhouse environment in Rijswijk, The Netherlands since April, 2014 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Goldmine Imp'. These characteristics in combination distinguish 'Goldmine Imp' as a new and distinct *Phlox* plant:

1. Upright plant habit.
2. Green and yellow variegated leaves with undulate margins.
3. Red purple-colored flowers.

Plants of the new *Phlox* differ from plants of the parent, 'Goldmine', primarily in leaf variegations colors. In addition, leaves of plants of the new *Phlox* plant have undulate margins whereas leaves of plants of 'Goldmine' have flat margins.

Plants of the new *Phlox* can be compared to plants of *Phlox* 'Kirchenfurst', not patented. In side-by-side comparisons plants of the new *Phlox* and 'Kirchenfurst' differed in the following characteristics:

1. Plants of the new *Phlox* were shorter than plants of 'Kirchenfurst'.
2. Plants of the new *Phlox* had variegated leaves with undulate margins whereas plants of 'Kirchenfurst' had non-variegated leaves with flat margins.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of a typical flowering plant of 'Goldmine Imp' grown in a container.

The photograph on the second sheet is a close-up view of typical leaves of 'Goldmine Imp'.

The photograph on the third sheet is a close-up view of a typical flowering plant of 'Goldmine Imp'.

DETAILED BOTANICAL DESCRIPTION

The aforementioned photographs and following observations, measurements and values describe plants grown during the summer in 1.5-liter containers in an outdoor nursery in Rijswijk, The Netherlands and under cultural practices typical of commercial *Phlox* production. During the production of the plants, day temperatures ranging from 14° C. to 30° C. and night temperatures ranging from 10° C. to 18° C. Plants were six months old when the photographs and description were taken. In the following description, color references are made to The Royal Horticultural Society Colour Chart, 2007 Edition, except where general terms of ordinary dictionary significance are used.

Botanical classification: *Phlox paniculata* 'Goldmine Imp'.

Parentage: Naturally-occurring whole plant mutation of the *Phlox paniculata* 'Goldmine', disclosed in U.S. Plant Pat. No. 12,070.

Propagation:

*Type*.—By vegetative cuttings.

*Time to initiate roots, summer*.—About ten days at temperatures about 25° C.

*Time to produce a rooted plant, summer*.—About 30 days at temperatures about 18° C. to 25° C.

*Root description*.—Medium thickness, fleshy; white in color.

*Rooting habit*.—Freely branching; sparse.

Plant description:

*Plant and growth habit*.—Upright plant habit; narrow inverted triangle; moderately vigorous to vigorous growth habit.

*Branching habit*.—Moderately freely basal branching habit.

*Plant height*.—About 53.5 cm.

*Plant width* (*spread*).—About 19.4 cm.

*Stem length* (*excluding inflorescence*).—About 42 cm.

*Stem diameter*.—About 4.5 mm.

*Internode length*.—About 3.1 cm.

*Stem strength*.—Strong.

*Stem texture*.—Smooth, glabrous.

*Stem color*.—Close to 144B and 145A.

Leaf description:

*Arrangement*.—Opposite, simple.

*Length*.—About 10.5 cm.

*Width*.—About 3.7 cm.

*Shape*.—Elliptic.

*Apex*.—Acute; moderately curved downward.

*Base*.—Truncate.

*Margin*.—Entire; strongly undulate.

*Texture, upper and lower surfaces*.—Smooth, glabrous; rugose.

*Venation pattern*.—Pinnate.

*Color*.—Developing leaves, upper surface: Centers, close to 143A; towards the margins, close to 151B. Developing leaves, lower surface: Centers, close to 147B; towards the margins, close to 151A. Fully expanded leaves, upper surface: Centers, close to between N137A and 146A; towards the margins, close to 12A; venation, close to 144B to 144C. Fully expanded leaves, lower surface: Centers, close to 147B; towards the margins, close to 11A; venation, close to 144C.

*Petioles*.—Length: About 2 mm. Diameter: About 2 mm by 3 mm. Texture, upper and lower surfaces: Smooth, glabrous. Color, upper and lower surfaces: Close to 144C.

Flower description:

*Flower type and flowering habit*.—Single salverform flowers arranged in terminal panicles; flowers face upright and outwardly; panicles roughly hemispherical in shape; freely flowering habit with about 100 flowers developing per inflorescence.

*Fragrance*.—Moderate; sweet and pleasant.

*Natural flowering season*.—Plants begin flowering about 20 weeks after planting; in the garden plants flower continuously from July to September in The Netherlands.

*Postproduction longevity*.—Flowers last about ten days on the plant; flowers not persistent.

*Flower buds*.—Height: About 1.5 cm. Diameter: About 3 mm. Shape: Narrowly elliptic. Color: Towards the base, close to 145C tinged with close to 187A; towards the apex, close to N81B.

*Inflorescence height*.—About 11.5 cm.

*Inflorescence diameter*.—About 9.3 cm.

*Flower diameter*.—About 2.9 cm.

*Flower depth* (*height*).—About 2.3 cm.

*Petals*.—Quantity per flower and arrangement: Typically five in a single whorl; petals fused at the base into a narrow tube. Length: About 3.5 cm (lower 2.2 cm fused into a tube). Lobe width: About 1.4 cm. Lobe shape: Spatulate. Apex: Rounded. Margin: Entire. Texture, upper and lower surfaces: Smooth, glabrous; velvety. Color: Developing and fully expanded petals, upper surface: Darker and more intense than close to N74A; towards the throat, close to 59B; throat, close to 72B. Developing and fully expanded petals, lower surface: Close to 72B; tube, close to N81A.

*Sepals*.—Quantity per flower and arrangement: Typically five in a single whorl, fused towards the base; calyx, campanulate in shape. Length: About 9 mm. Width: About 2 mm. Shape: Lanceolate. Apex: Narrowly apiculate. Margin: Entire. Texture, upper and lower surfaces: Smooth, glabrous. Color: Developing sepals, upper surface: Close to 144C slightly tinged with close to N186C. Developing sepals, lower surface: Close to 145C tinged with close to 187A. Fully expanded sepals, upper surface: Close to 144C very slightly tinged with close to N186C. Fully expanded sepals, lower surface: Close to 145C slightly tinged with close to 187A.

*Peduncles*.—Length: Main peduncle, about 8.1 cm; lateral peduncles, about 3.4 cm. Diameter: Main peduncle, about 2.5 mm; lateral peduncles, about 2 mm. Angle: Main peduncle, erect; lateral peduncles, about 35° from vertical. Strength: Strong. Texture: Smooth, glabrous. Color: Close to 145A.

*Pedicels*.—Length: About 3.5 mm. Diameter: About 1 mm. Angle: Erect to about 60° from vertical. Strength: Strong. Texture: Smooth, glabrous. Color: Close to 145A.

*Reproductive organs*.—Stamens: Quantity per flower: Typically five. Filament length: About 1 mm. Filament color: Close to 72B. Anther shape: Oblong. Anther length: About 1.5 mm. Anther color: Close to 8D. Pollen amount: Moderate. Pollen color: Close to 11D. Pistils: Quantity per flower: One. Pistil length: About 1.8 cm. Stigma shape: Tri-parted. Stigma color: Close to 150C. Style length: About 1.7 cm. Style color: Close to N77A. Ovary color: Close to 144A.

*Seeds and fruits*.—Seed and fruit development have not been observed on plants of the new *Phlox*.

Disease & pest resistance: Plants of the new *Phlox* have not been noted to be resistant to pathogens and pests common to *Phlox* plants.

Garden performance: Plants of the new *Phlox* have been observed to have good garden performance and tolerate rain, wind, high temperatures about 35° C. and to be hardy to USDA Hardiness Zone 6.

It is claimed:

1. A new and distinct *Phlox* plant named 'Goldmine Imp' as illustrated and described.

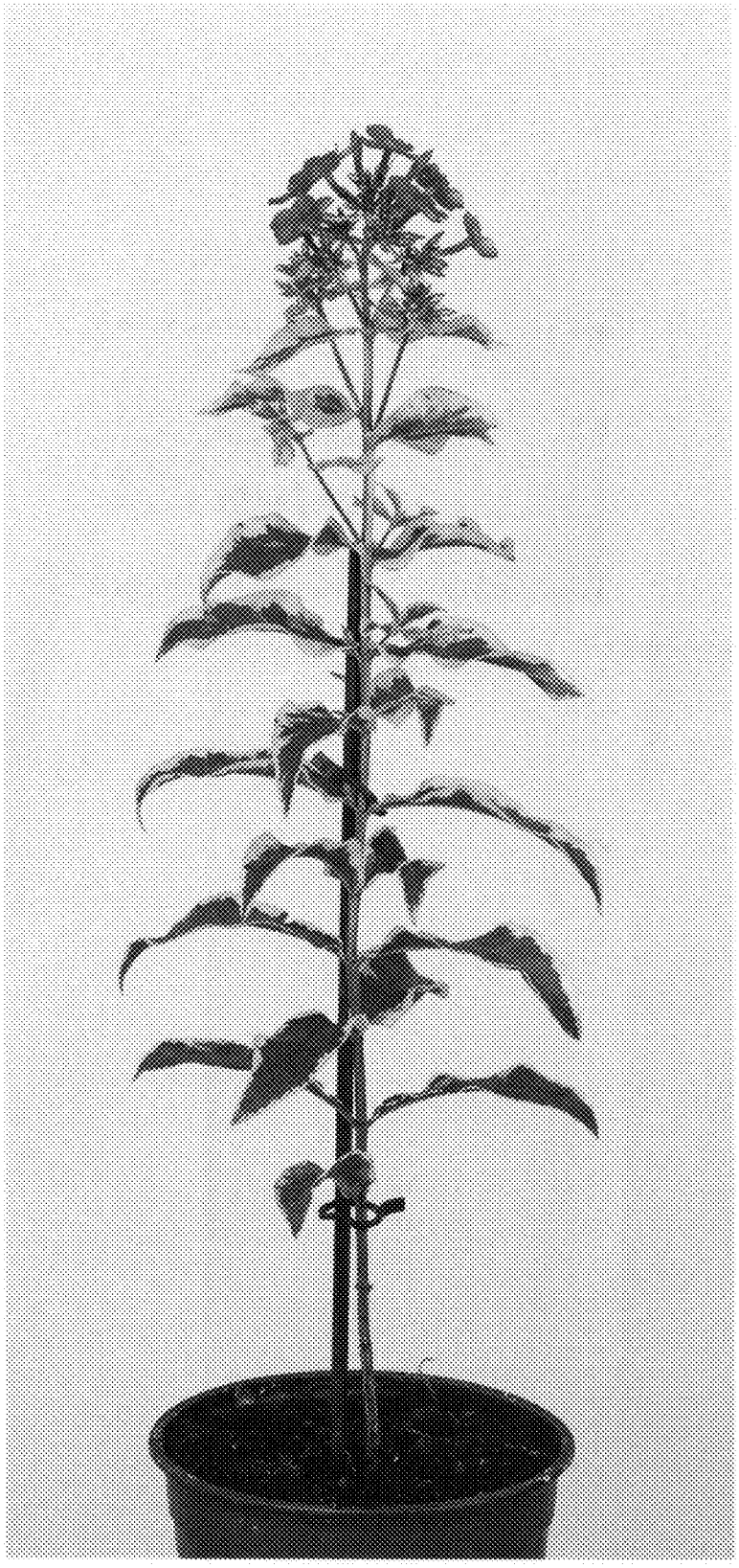

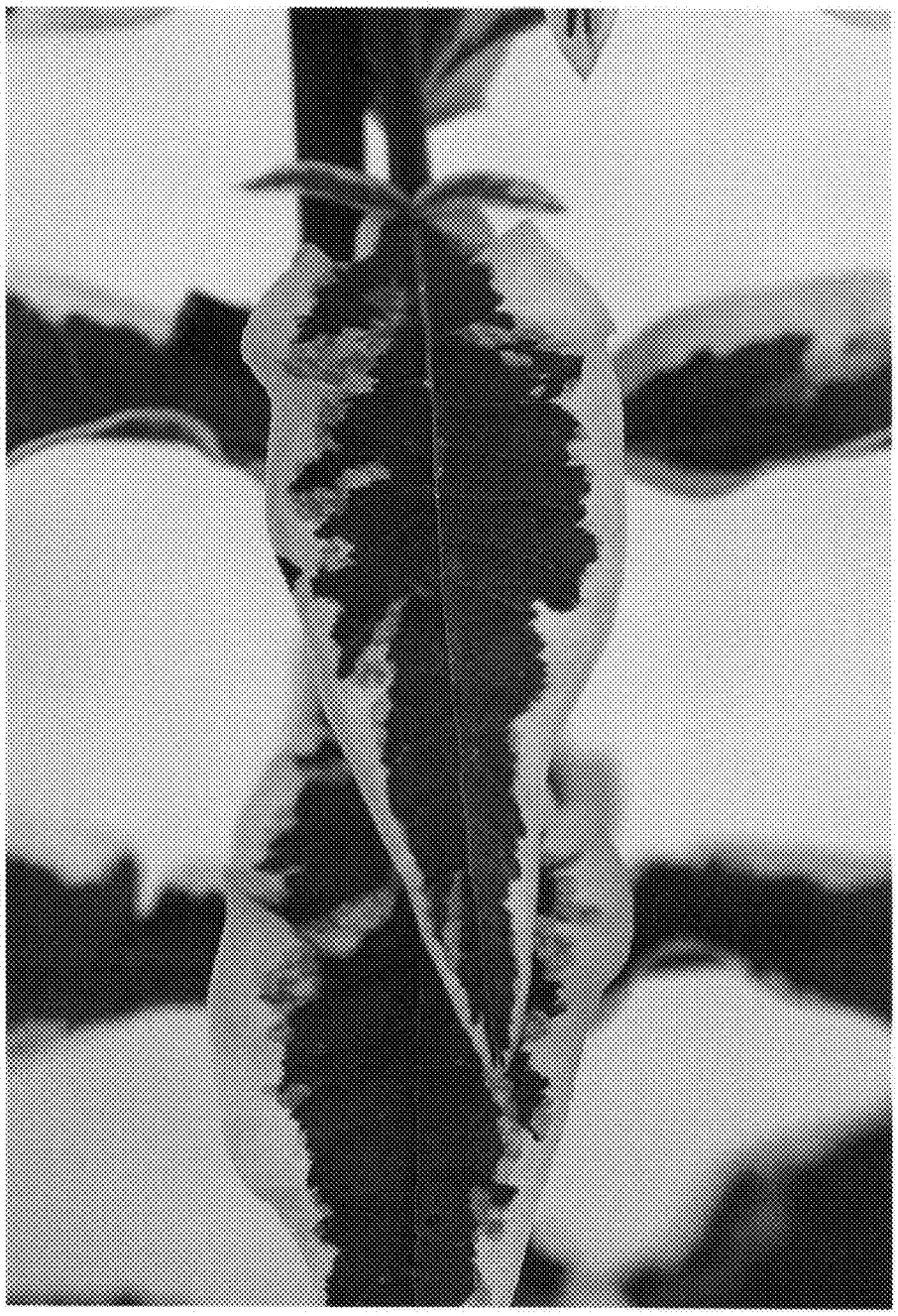

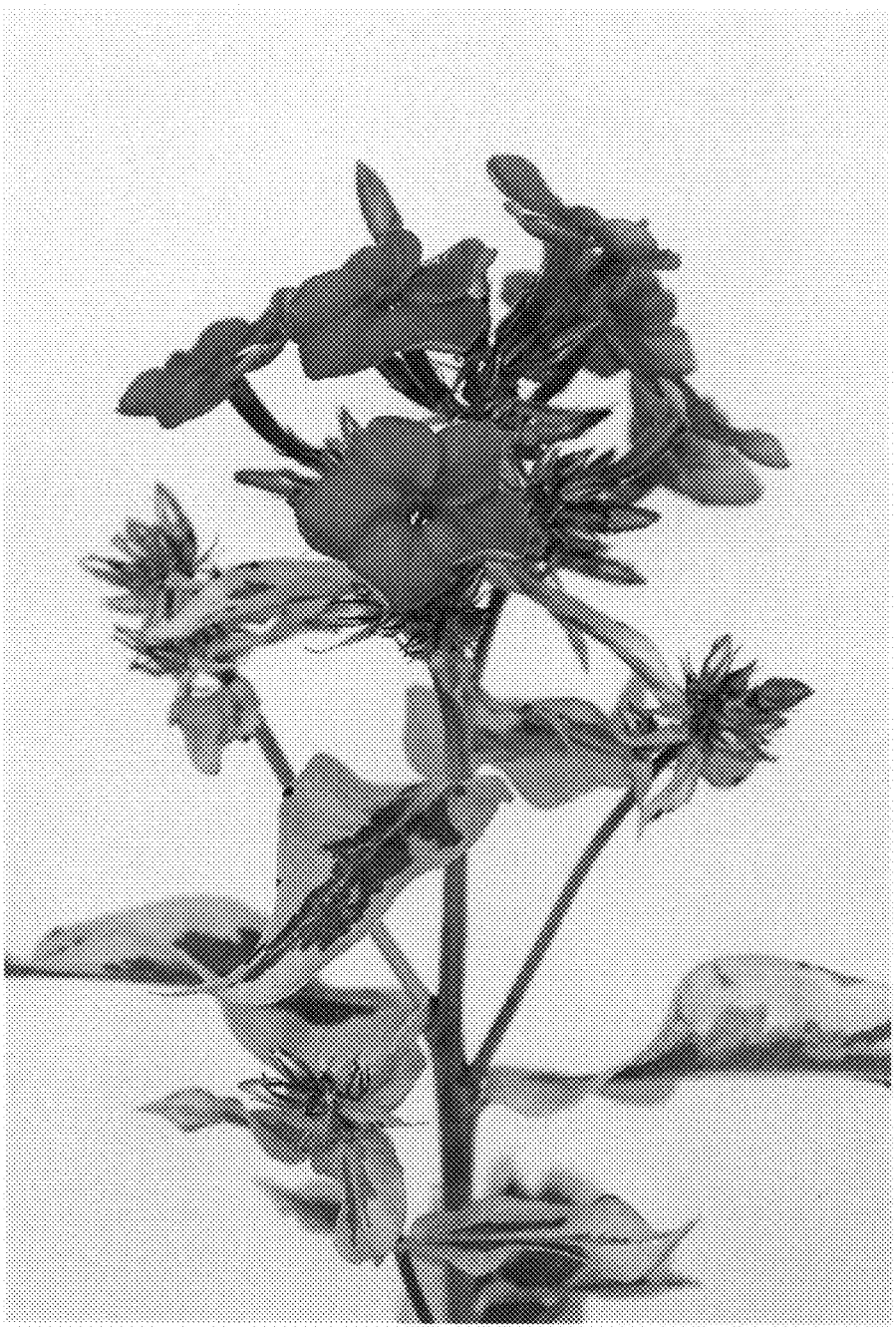

* * * * *